United States Patent [19]

Gaffar et al.

[11] Patent Number: 5,292,526
[45] Date of Patent: * Mar. 8, 1994

[54] ANTIBACTERIAL ANTIPLAQUE ANTICALCULUS ORAL COMPOSITION

[75] Inventors: Abdul Gaffar, Princeton; Nuran Nabi, North Brunswick; John Afflitto, Brookside, all of N.J.; Orum Stringer, Yardley, Pa.

[73] Assignee: Colgate-Palmolive Co., New York, N.Y.

[*] Notice: The portion of the term of this patent subsequent to Jan. 16, 2007 has been disclaimed.

[21] Appl. No.: 966,104

[22] Filed: Oct. 23, 1992

Related U.S. Application Data

[60] Division of Ser. No. 657,885, Feb. 19, 1991, Pat. No. 5,180,578, which is a continuation of Ser. No. 398,605, Aug. 25, 1989, abandoned, which is a continuation-in-part of Ser. No. 346,258, May 1, 1989, Pat. No. 5,043,154, which is a continuation of Ser. No. 8,901, Jan. 30, 1987, abandoned.

[51] Int. Cl.$^5$ .......................... A61K 7/16; A61K 7/18
[52] U.S. Cl. ........................................ 424/49; 424/52; 424/57
[58] Field of Search ........................... 424/49–58

[56] References Cited

U.S. PATENT DOCUMENTS

| | | | |
|---|---|---|---|
| 4,767,751 | 8/1988 | Davis | 514/179 |
| 4,835,002 | 5/1989 | Wolf et al. | 426/590 |
| 4,927,625 | 5/1990 | Duckworth | 424/52 |
| 4,933,173 | 6/1990 | Bristow et al. | 424/54 |
| 4,935,227 | 6/1990 | Duckworth | 424/52 |
| 4,940,701 | 7/1990 | Davis | 514/179 |
| 4,971,788 | 11/1990 | Tabibi et al. | 424/49 |
| 4,985,236 | 1/1991 | Ibrahim et al. | 424/52 |
| 4,988,499 | 1/1991 | Bristow et al. | 424/52 |
| 4,992,259 | 2/1991 | Schiraldi et al. | 424/49 |
| 5,015,466 | 5/1991 | Parran et al. | 424/52 |
| 5,015,467 | 5/1991 | Smitherman | 424/52 |
| 5,019,373 | 5/1991 | Carter et al. | 424/52 |
| 5,064,613 | 12/1991 | Higgs et al. | 422/16 |
| 5,096,701 | 3/1992 | White et al. | 424/52 |
| 5,096,702 | 3/1992 | Rolla et al. | 424/52 |
| 5,130,122 | 7/1992 | Tabibi et al. | 424/49 |
| 5,145,667 | 9/1992 | Ibrahim et al. | 424/52 |
| 5,162,378 | 11/1992 | Guthauser | 514/785 |
| 5,174,995 | 12/1992 | Davis | 424/400 |
| 5,176,900 | 1/1993 | White et al. | 424/52 |
| 5,180,578 | 1/1993 | Gaffar et al. | 424/52 |
| 5,188,822 | 2/1993 | Viccaro et al. | 424/52 |
| 5,190,915 | 3/1993 | Behan et al. | 512/2 |
| 5,192,530 | 3/1993 | Gaffar et al. | 424/52 |
| 5,246,918 | 9/1993 | Behan et al. | 512/2 |

*Primary Examiner*—Shep K. Rose
*Attorney, Agent, or Firm*—Robert L. Stone; Murray M. Grill

[57] ABSTRACT

An oral composition such as a dentifrice, mouthwash, lozenge or chewing gum containing a polyphosphate anticalculus agent, such as tetraalkali metal pyrophosphate and antibacterial antiplaque agent compatible therewith. The antiplaque agent is a substantially water-insoluble noncationic antibacterial agent such as 2,4,4'-trichloro-2'-hydroxydiphenyl ether (Triclosan). Antiplaque effectiveness is optimized by the presence of an antibacterial-enhancing agent which enhances delivery of said antibacterial agent to, and retention thereof on, oral surfaces.

33 Claims, No Drawings

ANTIBACTERIAL ANTIPLAQUE ANTICALCULUS ORAL COMPOSITION

The application is a division of application Ser. No. 07/657,885, filed Feb. 19, 1991, now U.S. Pat. No. 5,180,578 issued Jan. 19, 1993, which is a continuation of application Ser. No. 07/398,605, filed Aug. 25, 1989, now abandoned which is a continuation-in-part of application Ser. No. 346,258, filed May 1, 1989 now U.S. Pat. No. 5,043,154, granted Aug. 27, 1991, which is a continuation of application Ser. No. 8901, filed Jan. 30, 1987 now abandoned.

This invention relates to an antibacterial antiplaque anticalculus oral composition. More particularly, it relates to an oral composition containing a polyphosphate anticalculus (that is, antitartar) agent and a compatible antibacterial agent effective to inhibit plaque, wherein antiplaque effectiveness is optimized by the presence of an antibacterial-enhancing agent which enhances the delivery of said antibacterial agent to, and retention thereof on, oral surfaces.

In U.S. Pat. Nos. 4,627,977 to Gaffar et al; 4,515,772 to Parran et al; and 4,323,551 to Parran, oral compositions are described which include various polyphosphate compounds. In the patent to Gaffar et al, a linear molecularly dehydrated polyphosphate salt is employed in conjunction with a fluoride ion-providing source and a synthetic linear polymeric polycarboxylate to inhibit calculus formation. In copending U.S. patent application Ser. No. 169,915, filed Mar. 18, 1988, anticalculus effectiveness is optimized with a reduced amount of the linear molecularly dehydrated polyphosphate salt in conjunction with the fluoride ion-providing source and increased amount of the synthetic linear polymeric polycarboxylate.

In the patents to Parran et al and to Parran, water soluble dialkali metal pyrophosphate alone or mixed with tetraalkali metal pyrophosphate is employed.

Oral compositions which inhibit calculus formation on dental surfaces are highly desirable since calculus is one of the causative factors in periodontal conditions. Thus, its reduction promotes oral hygiene.

Dental plaque is a precursor of calculus. Unlike calculus, however, plaque may form on any part of the tooth surface, particularly including at the gingival margin. Hence, besides being unsightly, it is implicated in the occurrence of gingivitis.

Accordingly, it would be highly desirable to include antimicrobial agents which have been known to reduce plaque in oral compositions containing anticalculus agents. Indeed, this has been described in U.S. Pat. No. 4,022,550 to Vinson et al, wherein a compound providing zinc ions as an anticalculus agent is admixed with an antibacterial agent effective to retard the growth of plaque bacteria. A wide variety of antibacterial agents are described with the zinc compounds including cationic materials such as guanides and quaternary ammonium compounds as well as non-cationic compounds such as halogenated salicylanilides and halogenated hydroxydiphenyl ethers.

Hitherto, the cationic antibacterial materials such as chlorhexidine, benzethonium chloride and cetyl pyridinium chloride have been the subject of greatest investigation as antibacterial antiplaque agents. However, in spite of their being used in conjunction with zinc anticalculus agent, they are not effective when used with anionic materials such as polyphosphate anticalculus agent. This ineffectiveness is considered to be quite surprising as polyphosphates are chelating agents and the chelating effect has previously been known to increase the efficacy of cationic antibacterial agents. (see e.g. *Disinfection, sterilization and Preservation*, 2nd Ed., Black, 1977, Page 915 and *Inhibition and Destruction of the Microbial Cell*, Hugo, 1971, Page 215). Indeed, quaternary ammonium compound is present in the plaque control mouthwash containing pyrophosphate of U.S. Pat. No. 4,323,551 to Parran and bis-biguanide antiplaque agent is suggested in the anticalculus pyrophosphate oral composition of U.S. Pat. No. 4,515,772-Parran et al.

In view of the surprising incompatibility of cationic antibacterial agents with polyphosphates present as anticalculus agents, it was quite unexpected that other antibacterial agents would be effective.

It is an advantage of this invention that certain antibacterial agents are effective in anticalculus oral compositions containing a linear molecularly dehydrated polyphosphate salt, a fluoride-ion-providing source and the aforementioned antibacterial-enhancing agent to inhibit plaque formation.

It is a further advantage of this invention that a composition is provided which is effective to reduce calculus formation and optimize plaque reduction.

It is a further advantage of this invention that an antiplaque, anticalculus oral composition is provided which is effective to reduce the occurrence of gingivitis.

Additional advantages of this invention will be apparent from consideration of the following specification.

In accordance with certain of its aspects this invention relates to an oral composition comprising in an orally acceptable vehicle, an effective anticalculus amount of material comprising about 0.1-3% by weight of at least one linear molecularly dehydrated polyphosphate salt as anticalculus agent, an effective antiplaque amount of a substantially water insoluble noncationic antibacterial agent and up to about 4% by weight of an antibacterial-enhancing agent which enhances the delivery of said antibacterial to, and retention thereof on, oral surfaces, the weight ratio of polyphosphate ion to antibacterial-enhancing agent ranging from about 1.6:1 to about 2.7:1, preferably about 1.7:1 to about 2.3:1 and most preferably about 1.9:1 to about 2:1 For instance, when 2% tetrasodium pyrophosphate (TSPP) is employed (providing about 1.3% of pyrophosphate ion) with 2.5% of the antibacterial-enhancing agent, a highly desirable weight ratio of about 1.9:1 is provided.

The aspects of invention described below are also within this disclosure:

An invention aspect of oral composition comprising an orally acceptable vehicle, an anti-bacterial-enhancing agent as defined herein, and polyphosphate anticalculus agent, the said polyphosphate anticalculus agent being a mixture of potassium and sodium salts, the ratio of potassium to sodium in the said composition being in the range of up to less than 3:1, e.g. from 0.37:1 to 1.04:1.

A further invention aspect of an oral composition comprising an orally acceptable vehicle, an anti-bacterial-enhancing agent (as defined herein), the anti-bacterial-enhancing agent being free from or substantially free from water soluble alkali metal or ammonium synthetic anionic linear polymeric polycarboxylate salt having a molecular weight of 1,000 to 1,000,000, and polyphosphate anticalculus agent.

A further invention aspect of an oral composition comprising an orally acceptable vehicle, a substantially water insoluble non-cationic anti-bacterial agent, an anti-bacterial agent ranging from in excess of 0.72:1 to less than 4:1, e.g. from 1:1 to 3.5:1, especially from about 1.6:1 to 2.7:1.

A further invention aspect of an oral composition comprising an orally acceptable vehicle, an anti-bacterial-enhancing agent (as defined herein) and polyphosphate anticalculus agent with the proviso that the composition is free from or substantially free from tetrasodium pyrophosphate or a combination of tetrapotassium pyrophosphate and tetrasodium pyrophosphate in which the ratio of potassium to sodium pyrophosphate is 3:1 or in excess of 3:1.

A further invention aspect of an oral composition comprising an orally acceptable vehicle, a substantially water insoluble non-cationic anti-bacterial agent, an anti-bacterial-enhancing agent (as defined herein) and polyphosphate anticalculus agent with the proviso that the non-cationic anti-bacterial agents disclosed in Published GB Application No. 2200551 are excluded from the scope of this aspect. Published GB Application No. 2200551 corresponds to ancestor application Ser. No. 07/008,901.

A further invention aspect of an oral composition comprising an orally acceptable vehicle, a substantially water insoluble non-cationic anti-bacterial agent and polyphosphate anticalculus agent, with the proviso that the composition is free from or substantially free from tetrasodium pyrophosphate or a combination of tetrapotassium pyrophosphate and tetrasodium pyrophosphate including the ratio of potassium to sodium pyrophosphate is 3:1 or in excess of 3:1.

A further invention aspect of an oral composition comprising an orally acceptable vehicle, a substantially water insoluble non-cationic anti-bacterial agent, an anti-bacterial-enhancing agent (as defined herein), the anti-bacterial-enhancing agents being free or substantially free from water soluble alkali metal or ammonium synthetic anionic linear polymeric polycarboxylate salt having a molecular weight of 1,000 to 1,000,000, and polyphosphate anticalculus agent, with the proviso that the composition is free from or substantially free from tetrasodium pyrophosphate or a combination of tetrapotassium pyrophosphate and tetrasodium pyrophosphate or a combination of tetrapotassium pyrophosphate and tetrasodium pyrophosphate in which the ratio of potassium to sodium pyrophosphate is 3:1 or in excess of 3:1.

A further invention aspect of an oral composition comprising an orally acceptable vehicle, an anti-bacterial-enhancing agent (as defined herein), the said composition containing potassium and sodium salts or ions, the ratio of potassium to sodium in the said composition being in the range of up to less than 3:1, e.g. from 0.37:1 to 1.04:1.

A further invention aspect of an oral composition comprising an orally acceptable vehicle, a substantially water insoluble non-cationic anti-bacterial agent, the said composition containing potassium and sodium salts or ions, the ratio of potassium to sodium in the said composition being in the range of up to less than 3:1 e.g. from 0.37:1 to 1.04:1.

A further invention aspect of an oral composition comprising an orally acceptable vehicle, a substantially water insoluble non-cationic anti-bacterial agent, the said composition containing potassium and sodium salts or ions, the ratio of potassium to sodium in the said composition being in the range of up to less than 3:1, e.g. from 0.37:1 to 1.04:1.

A further invention aspect of an oral composition comprising an orally acceptable vehicle, a substantially water insoluble non-cationic anti-bacterial agent, an anti-bacterial-enhancing agent (as defined herein), the anti-bacterial enhancing agent being free from or substantially free from water soluble alkali metal or ammonium synthetic anionic linear polymeric polycarboxylate salt having a molecular weight of 1,000 to 1,000,000.

A further invention aspect of an oral composition comprising an orally acceptable vehicle, a substantially water insoluble non-cationic anti-bacterial agent in an amount of from 0.25% to less than 0.5% by weight and an anti-bacterial-enhancing agent (as defined herein).

A further invention aspect of an oral composition comprising an orally acceptable vehicle, a substantially water insoluble non-cationic anti-bacterial agent in an amount of from 0.25% to 0.35% and an anti-bacterial enhancing agent (as defined herein).

A further invention aspect of an oral composition comprising an orally acceptable vehicle, a substantially water insoluble non-cationic anti-bacterial agent in an amount of from 0.25% to 0.35% and polyphosphate anticalculus agent.

A further invention aspect of an oral composition comprising an orally acceptable vehicle, a substantially water insoluble non-cationic anti-bacterial agent in an amount of from 0.25% to 0.35% and polyphosphate anticalculus agent, the said polyphosphate anticalculus agent being a mixture of potassium and sodium salts, the ratio of potassium in the said composition being in the range of up to less than 3:1, e.g. from 0.37:1 to 1.04:1.

A further invention aspect of an oral composition comprising an orally acceptable vehicle, a substantially water insoluble non-cationic anti-bacterial agent in an amount of from 0.25% to 0.35% and polyphosphate anticalculus agent, with the proviso that the composition is free from or substantially free from tetrasodium polyphosphate or a combination of tetrapotassium pyrophosphate and tetrasodium pyrophosphate in which the ratio of potassium to sodium pyrophosphate is 3:1 or in excess of 3.1.

A further invention aspect of an oral composition comprising an orally acceptable vehicle, a substantially water insoluble non-cationic anti-bacterial agent, and anti-bacterial-enhancing agent (as defined herein), the said composition containing potassium and sodium salts or ions, the ratio of potassium to sodium in the said composition being in the range of from 0.37:1 to 1.04:1.

A further invention aspect of an oral composite comprising acceptable vehicle, a substantially water insoluble non-cationic anti-bacterial agent, an anti-bacterial-enhancing agent (as defined herein), and polyphosphate anticalculus agent, the said polyphosphate anticalculus agent being a mixture of potassium and sodium salts, the ratio of potassium to sodium in the said composition being in the range of up to less than 3:1, e.g. from 0.37:1 to 1.04:1.

A further invention aspect of an oral composition comprising an orally acceptable vehicle, siliceous polishing agent, about 0.25% to less than 0.5% by weight of a substantially water insoluble non-cationic anti-bacterial agent, and an anti-bacterial-enhancing agent (as defined herein).

A further invention aspect of an oral composition comprising an orally acceptable vehicle, a substantially water insoluble non-cationic anti-bacterial agent, and an anti-bacterial-enhancing agent as defined herein with the proviso that those anti-bacterial enhancing agents disclosed in published GB Application No. 2200551 are excluded from the scope of this aspect. Published GB Application No. 2200551 corresponds to ancestor Application S.N. 07/008,901.

Typical examples of antibacterial agents which are particularly desirable from considerations of antiplaque effectiveness, safety and formulation are:

Halogenated Diphenyl Ethers

2',4,4'-trichloro-2-hydroxy-diphenyl ether (Triclosan)
2,2'-dihydroxy-5,5'-dibromo-diphenyl ether.

Halogenated Salicylanilides

4',5-dibromosalicylanilide
3,4',5-trichlorosalcylanilide
3,4',5-tribromosalicylanilide
2,3,3',5-tetrachlorosalicylanilide
3,3,3',5-tetrachlorosalicylanilide
3,5-dibromo-3'-trifluoromethyl salicylanilide
5-n-octanoyl-3'-trifluoromethyl salicylanilide
3,5-dibromo-4'-trifluoromethyl salicylanilide
3,5-dibromo-3'-trifluoro methyl salicylanilide (Fluro-phene)

Benzoic Esters

Methyl—p-Hydroxybenzoic Ester
Ethyl—p-Hydroxybenzoic Ester
Propyl—p-Hydroxybenzoic Ester
Butyl—p-Hydroxybenzoic Ester

Halogenated Carbanilides 3,4,4'-trichlorocarbanilide
3-trifluoromethyl-4,4'-dichlorocarbanilide
3,3,4'-trichlorocarbanilide Phenolic Compounds (including phenol and its homologs, mono- and poly-alkyl and aromatic halo (e.g. F, Cl, Br, I.)phenols, resorcinol and catechol and their derivatives and bisphenolic compounds). Such phenolic compounds include, inter alia:

| Phenol and its Homologs | |
|---|---|
| 2 Methyl | - Phenol |
| 3 Methyl | - Phenol |
| 4 Methyl | - Phenol |
| 4 Ethyl | - Phenol |
| 2,4-Dimethyl | - Phenol |
| 2,5-Dimethyl | - Phenol |
| 3,4-Dimethyl | - Phenol |
| 2,6-Dimethyl | - Phenol |
| 4-n Propyl | - Phenol |
| 4-n-Butyl | - Phenol |
| 4-n-Amyl | - Phenol |
| 4-tert-Amyl | - Phenol |
| 4-n-Hexyl | - Phenol |
| 4-n-Heptyl | - Phenol |
| 2-Methoxy-4-(2-Propenyl) | - Phenol (Eugenol) |
| 2-Isopropyl-5-Methyl | - Phenol (Thymol) |
| Mono- and Poly-Alkyl and Aralkyl Halophenols | |
| Methyl | - p-Chlorophenol |
| Ethyl | - p-Chlorphenol |
| n-Propyl | - p-Chlorophenol |
| n-Butyl | - p-Chlorophenol |
| n-Amyl | - p-Chlorophenol |
| sec-Amyl | - p-Chlorophenol |
| n-Hexyl | - p-Chlorophenol |
| cyclohexyl | - p-Chlorophenol |
| n-Heptyl | - p-Chlorophenol |
| n-Octyl | - p-Chlorophenol |
| O-Chlorophenol | |
| Methyl | - o-Chlorophenol |
| Ethyl | - o-Chlorophenol |
| n-Propyl | |
| n-Butyl | - o-Chlorophenol |
| n-Amyl | - o-Chlorophenol |
| tert-Amyl | - o-Chlorophenol |
| n-Hexyl | - o-chlorophenol |
| n-Heptyl | - o-Chloropenol |
| p-Chlorophenol | |
| o-Benzyl | - p-Chlorophenol |
| o-Benzyl-m-methyl | - p-Chlorophenol |
| o-Benzyl-m,m-dimethyl | - p-Chlorophenol |
| o-Phenylethyl | - p-Chlorophenol |
| o-Phenylethyl-m-methyl | - p-Chlorophenol |
| 3-Methyl | - p-Chlorophenol |
| 3,5-Dimethyl | - p-Chlorophenol |
| 6-Ethyl-3-methyl | - p-Chlorophenol |
| 6-n-Propyl-3-methyl | - p-Chlorophenol |
| 6-iso-propyl-3-methyl | - p-Chlorophenol |
| 6-Ethyl-3,5-dimethyl | - p-Chlorophenol |
| 6-sec Butyl-3-methyl | - p-Chlorophenol |
| 2-iso-Propyl-3,5-dimethyl | - p-Chlorophenol |
| 6-Diethylmethyl-3-methyl | - p-Chlorophenol |
| 6-iso-Prop-2-ethyl-3-methyl | - p-Chlorophenol |
| 2-sec Amyl-3,5-dimethyl | - p-Chlorophenol |
| 2-Diethylmethyl-3,5-dimethyl | - p-Chlorophenol |
| 6-sec Octyl-3-methyl | - p-Chlorophenol |
| p-Bromophenol | |
| Methyl | - p-Bromophenol |
| Ethyl | - p-Bromophenol |
| n-Propyl | - p-Bromophenol |
| n-Butyl | - p-Bromophenol |
| n-Amyl | - p-Bromophenol |
| sec-Amyl | - p-Bromophenol |
| n-Hexyl | - p-Bromophenol |
| cyclohexyl | - p-Bromophenol |
| o-Bromophenol | |
| tert-Amyl | - o-Bromophenol |
| n-Hexyl | - o-Bromophenol |
| n-Propyl-m,m-Dimethyl | - o-Bromophenol |
| 2-Phenyl Phenol | |
| 4-Chloro-2-methyl phenol | |
| 4-chloro-3-methyl phenol | |
| 4-chloro-3,5-dimethyl phenol | |
| 2,4-dichloro-3,5-dimethyl phenol | |
| 3,4,5,6-tetrabromo-2-methylphenol | |
| 5-methyl-2-pentylphenol | |
| 4-isopropyl-3-methylphenol | |
| 5-chloro-2-hydroxydiphenyl methane | |
| Resorcinol and Its Derivatives | |
| Resorcinol | |
| Methyl | - Resorcinol |
| Ethyl | - Resorcinol |
| n-Propyl | - Resorcinol |
| n-Butyl | - Resorcinol |
| n-Amyl | - Resorcinol |
| n-Hexyl | - Resorcinol |
| n-Heptyl | - Resorcinol |
| n-Octyl | - Resorcinol |
| n-Nonyl | - Resorcinol |
| Phenyl | - Resorcinol |
| Benzyl | - Resorcinol |
| Phenylethyl | - Resorcinol |
| Phenylpropyl | - Resorcinol |
| p-Chlorobenzyl | - Resorcinol |
| 5-Chloro | -2,4-Dihydroxydiphenyl Methane |
| 4'-Chloro | -2,4-Dihydroxydiphenyl Methane |
| 5-Bromo | -2,4-Dihydroxydiphenyl Methane |
| 4'-Bromo | -2,4-Dihydroxydiphenyl Methane |

BISPHENOLIC COMPOUNDS

Bisphenol A 2,2'-methylene bis (4-chlorophenol)

2,2'-methylene bis (3,4,6-trichlorophenol) (hexachlorophene)
2,2'-methylene bis (4-chloro-6-bromophenol)
bis (2-hydroxy-3,5-dichlorophenyl) sulfide
bis (2-hydroxy-5-chlorobenzyl) sulfide The antibacterial agent is present in the oral composition in an effective antiplaque amount, typically about 0.01–5% by weight, preferably about 0.03–1% and most preferably about 0.25–0.5%. The antibacterial agent is substantially water-insoluble, meaning that its solubility is less than about 1% by weight in water at 25° C. and may be even less than about 0.1%. If an ionizable group is present solubility is determined at a pH at which ionization does not occur.

The preferred halogenated diphenyl ether is Triclosan. The preferred phenolic compounds are phenol, 2,2'methylene bis (4-chloro-6-bromophenol), thymol and eugenol. The most preferred antibacterial antiplaque compound is Triclosan. Triclosan is disclosed in aforementioned U.S. Pat. No. 4,022,880 as an antibacterial agent in combination with an anticalculus agent which provides zinc ions and in German Patent Disclosure 35 32 860 in combination with a copper compound. It is also disclosed as an antiplaque agent in a dentifrice formulated to contain a lamellar liquid crystal surfactant phase having a lamellar spacing of less than 6.0 nm and which may optionally contain a zinc salt in published European Patent Application 0161898 of Lane et al and in a dentifrice containing zinc citrate trihydrate in published European Patent Application 0161899 to Saxton.

The linear molecularly dehydrated polyphosphate salts operative herein as anticalculus agents are well known, being generally employed in the form of their wholly or partially neutralized water soluble alkali metal (e.g. potassium and preferable sodium) or ammonium salts, and any mixtures thereof. Representative examples include sodium hexametaphosphate, sodium tripolyphosphate, disodium diacid, trisodium monoacid and tetrasodium pyrophosphates, the corresponding potassium salts and the like.

Particularly desirable anticalculus agents are tetraalkali metal pyrophosphates, including mixtures thereof, such as tetrasodium pyrophosphate, tetrapotassium pyrophosphate and mixtures thereof. An anticalculus agent comprising about 2% by weight of the oral compositions of tetrasodium pyrophosphate is especially effective.

The antibacterial-enhancing agent (AEA) which enhances delivery of said antibacterial agent to, and retention thereof on, oral surfaces, is employed in amounts effective to achieve such enhancement within the range in the oral composition of about 0.05% to about 4%, preferably about 0.1% to about 3%, more preferably about 0.5% to about 2.5% by weight.

AEA polymeric materials of the present invention include those which can be characterized as having utility as dentifrice adhesives or fixatives or dental cements. For example, U.S. Pat. Nos. 4,521,551 and 4,375,036, each to Chang et al, describe commercially available copolymer of methylvinyl ether-maleic anhydride (Gantrez) as a denture fixative. However, there has not been recognition in the prior art that adhesives, fixatives or cements when applied in water-soluble or water-swellable form together with substantially water-insoluble non-cationic antibacterial antiplaque agents could enhance the antibacterial activity of such agents. Further, in U.S. Pat. No. 4,485,090 to Chang, Gantrez AN copolymer is mentioned among polymeric anionic membrane forming materials which attach to a tooth surface to form a hydrophobic barrier which reduces elution of a previously applied therapeutic caries prophylactic fluoride compound. Again, there is no recognition that such polymeric material could enhance the antibacterial activity of substantially water-insoluble non-cationic antibacterial antiplaque agents.

This AEA may be a simple compound, preferably a polymerizable monomer, more preferably a polymer, which latter term is entirely generic, including for example oligomers, homopolymers, copolymers of two or more monomers, ionomers, block copolymers, graft copolymers, cross-linked polymers and copolymers, and the like. The AEA may be natural or synthetic, and water insoluble or preferably water (saliva) soluble or swellable (hydratable, hydrogel forming). It has an (weight) average molecular weight of about 100 to about 1,000,000, preferably about 1,000 to about 1,000,000, more preferably about 2,000 or 2,500 to about 250,000 or 500,000.

The AEA ordinarily contains at least one delivery-enhancing group, which is preferably acidic such as sulfonic, phosphinic, or more preferably phosphonic or carboxylic, or salt thereof, e.g. alkali metal or ammonium, and at least one organic retention-enhancing group, preferably a plurality of both the delivery-enhancing and retention-enhancing groups, which latter groups preferably have the formula —$(X)_n$—R wherein X is O, N, S, SO, $SO_2$, P, PO or Si or the like, R is hydrophobic alkyl, alkenyl, acyl, aryl, alkaryl, aralkyl, heterocyclic or their inert-substituted derivatives, and n is zero or 1 or more. The aforesaid "inert-substituted derivatives", are intended to include substituents on R which are generally non-hydrophilic and do not significantly interfere with the desired functions of the AEA as enhancing the delivery of the antibacterial agent to, and retention thereof on, oral surfaces such as halo, e.g. Cl, Br, I, and carbo and the like. Illustrations of such retention-enhancing groups are tabulated below.

| n | X | —$(X)_n$R |
|---|---|---|
| 0 | — | methyl, ethyl, propyl, butyl, isobutyl, t-butyl, cyclohexyl, allyl, benzyl, phenyl, chlorophenyl, xylyl, pyridyl, furanyl, acetyl, benzoyl, butyryl, terephthaloyl, etc. |
| 1 | O | carboethoxy, carbobenzyloxy, etc. |
|   | N | ethylamino, diethylamino, propylamido, benzylamino, benzoylamido, phenylacetamido, etc. |
|   | S | thiobutyl, thioisobutyl, thioallyl, thiobenzyl, thiophenyl, thiopropionyl, phenylthioacetyl, thiobenzoyl, etc. |
|   | SO | butylsulfoxy, allylsulfoxy, benzylsulfoxy, phenylsulfoxy, etc. |
|   | $SO_2$ | butylsulfoxy, allysulfonyl, benzylsulfonyl, phenylsulfonyl, etc. |
|   | P | diethyphosphinyl, ethylvinylphosphinyl, ethylallylphosphinyl, ethylbenzylphosphinyl, ethylphenylphosphinyl, etc. |
|   | PO | diethylphosphinoxy, ethylvinylphosphinoxy, methylallylphosphinoxy, methylbenzyphosphinoxy, methylphenylphosphinoxy, etc. |
|   | Si | trimethysilyl, dimethylbutylsilyl, dimethylbenzylsilyl, dimethylvinylsilyl, dimethylallylsilyl, etc. |

As employed herein, the delivery-enhancing group refers to one which attaches or substantively, adhesively, cohesively or otherwise bonds the AEA (carrying the antibacterial agent) to oral (e.g. tooth and gum) surfaces, thereby "delivering" the antibacterial agent to such surfaces. The organic retention-enhancing group, generally hydrophobic, attaches or otherwise bonds the antibacterial agent to the AEA, thereby promoting retention of the antibacterial agent to the AEA and indirectly on the oral surfaces. In some instances, attachment of the antibacterial agent occurs through physical entrapment thereof by the AEA, especially when the AEA is a cross-linked polymer, the structure of which inherently provides increased sites for such entrapment. The presence of a higher molecular weight, more hydrophobic cross-linking moiety in the cross-linked polymer still further promotes the physical entrapment of the antibacterial agent to or by the cross-linked AEA polymer.

Preferably, the AEA is an anionic polymer comprising a chain or backbone containing repeating units each preferably containing at least one carbon atom and preferably at least one directly or indirectly pendant, monovalent delivery-enhancing group and at least one directly or indirectly pendant monovalent retention-enhancing group geminally, vicinally or less preferably otherwise bonded to atoms, preferably carbon, in the chain. Less preferably, the polymer may contain delivery-enhancing groups and/or retention-enhancing groups and/or other divalent atoms or groups as links in the polymer chain instead of or in addition to carbon atoms, or as cross-linking moieties.

It will be understood that any examples or illustrations of AEA's disclosed herein which do not contain both delivery-enhancing groups and retention enhancing groups may and preferably should be chemically modified in known manner to obtain the preferred AEA's containing both such groups and preferably a plurality of each such groups. In the case of the preferred polymeric AEA's, it is desirable, for maximizing substantivity and delivery of the antibacterial agent to oral surfaces, that the repeating units in the polymer chain or backbone containing the acidic delivery enhancing groups constitute at least about 10%, preferably at least about 50%, more preferably at least about 80% up to 95% or 100% by weight of the polymer.

According to a preferred embodiment of this invention, the AEA comprises a polymer containing repeating units in which one or more phosphonic acid delivery-enhancing groups are bonded to one or more carbon atoms in the polymer chain. An example of such an AEA is poly (vinyl phosphonic acid) containing units of the formula:

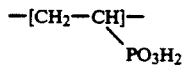   I which however does not contain a retention-enhancing group. A group of the latter type would however be present in poly (1-phosphonopropene) with units of the formula:

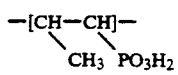   II

A preferred phosphonic acid-containing AEA for use herein is poly (beta styrene phosphonic acid) containing units of the formula:

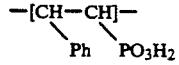   III wherein Ph is phenyl, the phosphonic delivery-enhancing group and the phenyl retention-enhancing group being bonded on vicinal carbon atoms in the chain, or a copolymer of beta styrene phosphonic acid with vinyl phosphonyl chloride having the units of the foregoing formula III alternating or in random association with units of formula I above, or poly (alpha styrene phosphonic acid) containing units of the formula:

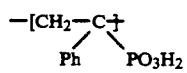   IV in which the delivery- and retention-enhancing groups are geminally bonded to the chain.

These styrene phosphonic acid polymers and their copolymers with other inert ethylenically unsaturated monomers generally have molecular weights in the range of about 2,000 to about 30,000, preferably about 2,500 to about 10,000, and are, with their methods of preparation disclosed and claimed in concurrently filed application Ser. No. 398,606, which disclosure is incorporated here. Such "inert" monomers do not significantly interfere with the intended function of any copolymer employed as an AEA herein.

Other phosphonic-containing polymers include, for example, phosphonated ethylene having units of the formula.

   (V)

where n may for example be an integer or have a value giving the polymer a molecular weight of about 3,000; and sodium poly (butene-4,4-diphosphonate) having units of the formula:

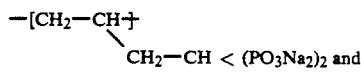   VI poly (allyl bis (phosphonoethyl) amine) having units of the formula:

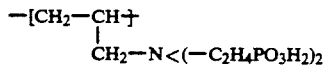   VII

Other phosphonated polymers, for example poly (allyl phosphono acetate), phosphonated polymethacrylate, etc. and the geminal diphosphonate polymers disclosed in EP Publication 0321233 may be employed herein as AEA's, provided of course that they contain or are modified to contain the above-defined organic retention-enhancing groups.

According to another preferred embodiment, the AEA comprises a synthetic anionic polymeric polycarboxylate which is also an inhibitor of alkaline phosphatase enzyme. Synthetic anionic polymeric polycarboxylates and their complexes with various cationic germicides, zinc and magnesium have been previously disclosed as anticalculus agents per se in, for example U.S. Pat. No. 3,429,963 to Shedlovsky; U.S. Pat. No. 4,152,420 to Gaffar; U.S. Pat. No. 3,956,480 to Dichter et al; U.S. Pat. No. 4,138,477 to Gaffar; and U.S. Pat. No. 4,183,914 to Gaffar et al. However, only in disclosure essentially corresponding to U.S. Pat. No. 4,627,977 to Gaffar et al is there described use of such polycarboxylates for inhibiting salivary hydrolysis of pyrophosphate anticalculus agents in combination with a compound providing a source of fluoride ion. It is to be understood that the synthetic anionic polymeric polycarboxylates so disclosed in these several patents when containing or modified to contain the retention-enhancing groups defined above are operative as AEA's in the compositions and methods of this invention and such disclosures are to that extent incorporated herein by reference thereto.

These synthetic anionic polymeric polycarboxylates are often employed in the form of their free acids or preferably partially or more preferably fully neutralized water soluble or water swellable (hydratable, gel/forming) alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000. These copolymers are available for example as Gantrez e.g. AN 139 (M.W. 500,000), A.N. 119 (M.W. 250,000); and preferably S-97 Pharmaceutical Grade (M.W. 70,000), of GAF Corporation.

Other AEA-operative polymeric polycarboxylates containing or modified to contain retention-enhancing groups include those disclosed in U.S. Pat. No. 3,956,480 referred to above, such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrollidone.

Additional operative polymeric polycarboxylates disclosed in above referred to U.S. Pat. No. 4,138,477 and 4,183,914, containing or modified to contain retention-enhancing groups include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are polymerized retention-enhancing group-containing olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorosorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers ordinarily contain sufficient carboxylic salt groups for water-solubility.

Also useful herein are so-called carboxyvinyl polymers disclosed as toothpaste components in U.S. Pat. No. 3,980,767 to Chown et al; U.S. Pat. No. 3,935,306 to Roberts et al; U.S. Pat. No. 3,919,409 to Perla et al; U.S. Pat. No. 3,911,904 to Harrison, and U.S. Pat. No. 3,711,604 to Colodney et al. They are commercially available for example under the trademarks Carbopol 934, 940 and 941 of B. V. Goodrich, these products consisting essentially of a colloidally water-soluble polymer of polyacrylic acid crosslinked with from about 0.75% to about 2.0% of polyallyl sucrose or polyallyl pentaerythritol as cross linking agent, the cross-linked structures and linkages providing the desired retention enhancement by hydrophobicity and/or physical entrapment of the antibacterial agent or the like. Polycarbophil is somewhat similar, being polyacrylic acid cross-linked with less than 0.2% of divinyl glycol, the lower proportion, molecular weight, and/or hydrophobicity of this cross-linking agent tending to provide decreased, or no, retention enhancement. 2,5-dimethyl-1,5-hexadiene exemplifies a more effective retention-enhancing cross-linking agent.

The synthetic anionic polymeric polycarboxylate component is most often a hydrocarbon with optional halogen and O-containing substituents and linkages as present in for example ester, ether and OH groups, and when present is generally employed in the instant compositions in approximate weight amounts of up to about 4% (generally at least about 0.05%).

The AEA may also comprise natural anionic polymeric polycarboxylates containing retention-enhancing groups. Carboxymethyl cellulose and other binding agents, gums and film-formers devoid of the above-defined delivery-enhancing and/or retention-enhancing groups are ineffective as AEA's.

As illustrative of AEA's containing phosphinic acid and/or sulfonic acid delivery enhancing groups, there may be mentioned polymers and copolymers containing units or moieties derived from the polymerization of vinyl or allyl phosphinic and/or sulfonic acids substituted as needed on the 1 or 2 (or 3) carbon atom by an organic retention-enhancing group, for example having the formula —(X)$_n$—R defined above. Mixtures of these monomers may be employed, and copolymers thereof with one or more inert polymerizable ethylenically unsaturated monomers such as those described above with respect to the operative synthetic anionic polymeric polycarboxylates. As will be noted, in these and other polymeric AEA's operative herein, usually only one acidic delivery-enhancing group is bonded to any given carbon or other atom in the polymer backbone or branch thereon. Polysiloxanes containing or modified to contain pendant delivery-enhancing groups and retention enhancing groups may also be employed as AEA's herein. Also effective as AEA's herein are ionomers containing or modified to contain delivery- and retention-enhancing groups. Ionomers are described on pages 546–573 or the Kirk-Othmer Encyclopedia of Chemical Technology, third edition, Supplement Volume, John Wiley * Sons, Inc. copyright 1984, which description is incorporated herein by reference. Also effective as AEA's herein, provided they contain are modified to contain retention-enhancing groups, are polyesters, polyurethanes and synthetic and natural polyamoides including proteins and proteinaceous materials such as collagen, poly (argenine) and other polymerized amino acids.

When the oral preparation is made by initially dissolving the polyphosphate and the antibacterial agent in humectant and surface active agent and adding thereto the AEA, especially the polycarboxylate, incrementally, the solution becomes clear and may be characterized as a "microemulsion". As the amount of the polycarboxylate increases such that the complete oral preparation contains at least about 2.2% by weight thereof, the solution becomes cloudy and may be characterized as a "macroemulsion". In such "macroemulsion" type compositions, the antiplaque effect of the antibacterial agent appears to be optimized.

In order to optimize the anticalculus effectiveness of the oral composition, inhibitors against enzymatic hydrolysis of the polyphosphate are desirably present. Such agents are an amount of a fluoride ion source sufficient to supply 25 ppm. to 5,000 ppm. of fluoride ions, and up to 3% or more of the synthetic anionic polymeric polycarboxylate having a molecular weight of about 1,000 to about 1,000,000, preferably about 30,000 to about 500,000.

The sources of fluoride ions, or fluorine-providing component, as acid phosphatase and pyrophosphatase enzyme inhibitor component, are well known in the art as anti-caries agents. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal, alkaline earth metal salts, for example, sodium fluoride, potassium fluoride, ammonium fluoride, calcium fluoride, a copper fluoride such as cuprous fluoride, zinc fluoride, barium fluoride such as cuprous fluoride, zinc fluoride, barium fluoride, sodium fluorosilicate, ammonium fluorosilicate, sodium fluorozirconate, ammonium fluorozirconate, sodium monofluorophosphate, aluminum mono- and difluorophosphate. and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type or oral preparation, but it must be a non-toxic amount, generally about 0.005 to about 3.0% in the preparation. In a dentifrice preparation, e.g. dental gel, toothpaste (including cream), toothpowder, or dental tablet, an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferably about 800 to about 1,500 ppm of fluoride ion.

Typically, in the cases of alkali metal fluorides, this component is present in an amount up to about 2% by weight, based on the weight of the preparation, and preferably in the range of about 0.05% to 1%. In the case of sodium monofluorophosphate, the compound may be present in an amount of about 0.1-3%, more typically about 0.76%.

In oral preparations such as mouthwashes, lozenges and chewing gum, the fluorine-providing compound is typically present in an amount sufficient to release up to about 500 ppm, preferably about 25 to 300 ppm by weight of fluoride ion. Generally about 0.005 to about 1.0 wt. % of such compound is present.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phsophate, etc.).

In certain other desirable form of this invention, the oral composition may be substantially solid or pasty in character, such as toothpowder, a dental tablet or a dentifrice, that is a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminum silicate, zirconium silicate, silica, bentonite, and mixtures thereof. Other suitable polishing material include the particulate thermosetting resins described in U.S. Pat. No. 3,070,510, issued Dec. 15, 1962, such as melamine-, phenolic, and urea-formaldehydes, and cross-linked polyepoxides and polyesters. Preferred polishing materials include crystalline silica having particle sized of up to about 5 microns, a mean particle size of up to about 1.1 microns, and a surface area of up to about 50,000 $cm.^2/gm.$, silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal alumino-silicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510–511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts ranging from about 10% to about 75% in toothpaste, and from about 70% to about 99% in toothpowder. In toothpastes, when the polishing material is silicious in nature, it is generally present in amount of about 10–30% by weight. Other polishing materials are typically present in amount of about 30–75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5–30 wt. % of water, 0 to about 70 wt. % of glycerine and about 20–80 wt. % of sorbitol are preferably employed.

Toothpastes, creams and gels typically contain a natural or synthetic thickener or gelling agent in proportions of about 0.1 to about 10, preferably about 0.5 to about 5 wt. %. A suitable thickener is synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244).

In some dentifrices prepared in accordance with the present invention particularly when more than about 0.35% by weight of the water insoluble antibacterial agent is employed and a siliceous polishing agent is present in amount of less than about 30% by weight, it may be desirable to include an agent which dissolves the antibacterial agent. Such solubilizing agents include humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, a jar of mouthrinse will have a label describing it, in substance, as a mouthrinse or mouthwash and having directions for its use; and a toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the anticalculus agent and antiplaque agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged a marked effect in the inhibition of acid formation in the oral cavity due to carbohydrates breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

Surface active agent is typically present in amount of about 0.1–5% by weight, preferably about 1–2.5%. It is noteworthy, that surface active agent may assist in the dissolving of the noncationic antibacterial agent and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, generally soluble, which would complex with active components of the instant invention are to be avoided.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine and the like. Suitably, flavor and sweetening agents may each or together comprise from about 0.1% to 5% more of the preparation. Moreover, flavor oil appears to aid the dissolving of the antibacterial agent.

In the preferred practice of this invention an oral composition according to this invention such as a mouthwash or dentifrice containing the composition of the present invention is preferably applied regularly to dental enamel, such as every day or every second or third day or preferably from 1 to 3 times daily, at a pH of about 4.5 to about 9, generally about 5.5 to about 8, preferably about 6 to 8, for at least 2 weeks up to 8 weeks or more up to lifetime.

The compositions of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticizers or softeners, sugar or other sweeteners or such as glucose, sorbitol and the like.

The following examples are further illustrative of the nature of the present invention, but it is understood that the invention is not limited thereto. All amounts and proportions referred to herein and in the appended claims are by weight unless otherwise indicated.

The following Examples, the agent Triclosan, 2,4,4'-trichloro-2'-hydroxydiphenyl ether is indicated as "TCHE"; sodium lauryl sulfate is indicated as "SLS"; the copolymer of maleic anhydride and methyl vinyl ether available from GAF Corporation as "Gantrez S-97" is identified as "Gantrez"; tetrasodium pyrophosphate is identified as "pyrophosphate"; and sodium fluoride is identified as "NaF".

EXAMPLE 1

The adsorption to and release from tooth minerals for antiplaque/antitartar efficacy of agents is assessed by adsorption of antibacterial agent to saliva coated tooth mineral hydroxyapatite disk in the presence of pyrophosphate and differing amounts of polycarboxylate.

The formulations of the toothpastes evaluated are:

|  | Parts by Weight | |
|---|---|---|
|  | A | B |
| Glycerine | 10.00 | 10.00 |
| Iota-carrageenan | 0.750 | 0.750 |
| Sorbitol (70% solution) | 30.000 | 30.000 |
| Propylene Glycol | 0.500 | 0.500 |
| Gantrez (13.02% solution) | 19.000 | 15.500 |
| Titanium dioxide | 0.500 | 0.500 |
| Water (deionized) | 9.957 | 13.457 |
| NaF | 0.243 | 0.243 |
| Sodium Saccharine | 0.300 | 0.300 |
| Pyrophosphate | 2.000 | 2.000 |
| Sodium hydroxide (50%) | 1.000 | 1.000 |
| Silica polishing agent (Zeodent 113) | 20.000 | 20.000 |
| Silica Thickener (Sylodent 15) | 2.500 | 2.500 |
| Flavor oil | 0.950 | 0.950 |
| TCHE | 0.300 | 0.300 |
| SLS | 2.000 | 2.000 |

Gantrez is present as A.I. in amount of 2.5 parts in toothpaste A and 2.0 parts in toothpaste B.

For the test of delivery of antibacterial agent to a saliva coated hydroxyapatite disk, hydroxtapatite (HA) obtained from the Monsanto Co. is washed extensively with distilled water, collected by vacuum filtration, and permitted to dry overnight at 37° C. The dried HA is ground into a powder with a mortar and pestle. 150.00 mgs of HA are placed into the chamber of a KBr pellete die (Barnes Analytical, Stanford, Conn.) and compressed for 6 minutes at 10,000 pounds in a Carver Laboratory press. The resulting 13 mm disks are sintered for 4 hours at 800° C. in a Thermolyne furnace. Parafilm stimulated whole saliva is collected into a ice-chilled glass beaker. The saliva is clarified by centrifugation at 15,000×g (times gravity) for 15 minutes at 4° C. Sterilization of the clarified-saliva is done at 4° C. with stirring by irradiation of the sample with UV light for 1.0 hour.

Each sintered disk is hydrated with sterile water in a polyethylene test tube. The water is then removed and replaced with 2.00 ml of saliva. A salivary pellicle is formed by incubating the disk overnight at 37° C. with continuous shaking in a water bath. After this treatment, the saliva is removed and the disks are treated with 1.00 ml of a solution containing antibacterial agent (triclosan) in a dentifrice liquid phase solution and incubated at 37° C. with continuous shaking in the water bath. After 30 minutes, the disk is transferred into a new tube and 5.00 ml of water are added followed by shaking the disk gently with a Vortex. The disk is then transferred into a new tube and the washing procedure repeated twice. Finally, the disk is transferred carefully into a new tube to avoid co-transfer of any liquid along with the disk. Then 1.00 ml of methanol is added to the disk and shaken vigorously with a Vortex. The sample is left at room temperature for 30 minutes to extract adsorbed triclosan in the methanol. The methanol is then aspirated and clarified by centrifugation in a Beckman Microfuge 11 at 10,000 rpm for 5 minutes. After this treatment, the methanol is transferred into HPLC(high performance liquid chromatography) vials for determination of antibacterial agent concentration. Triplicate samples are used in all experiments.

The Table below summarizes the data:

TABLE

| Toothpaste | Delivery of TCHE to Saliva Coated Hydroxyapatite Disc in Micrograms |
|---|---|
| A | 130 |
| B | 30 |

The data indicates that with the increasing amount of Gantrez (Toothpaste A) there is a very great increase in delivery of TCHE to saliva coated tooth minerals.

EXAMPLE 2

The following toothpaste is effective as an antiplaque and anticalculus composition:

|  | Parts by Weight |
|---|---|
| Sorbitol (70%) | 22.00 |
| Irish Moss | 1.00 |
| Sodium Hydroxide (50) | 1.00 |
| Gantrez (13.02% solution) | 19.00 |
| Water (deionized) | 2.69 |
| Sodium Monofluorophosphate | 0.76 |

-continued

|  | Parts by Weight |
| --- | --- |
| Sodium saccharine | 0.30 |
| Pyrophosphate | 2.00 |
| Hydrated alumina | 48.00 |
| Flavor oil | 0.95 |
| TCHE | 0.30 |
| SLS | 2.00 |

EXAMPLE 3

| Mouthrinse | Parts |
| --- | --- |
| Tetrasodium Pyrophosphate | 2.00 |
| Gantrez S-97 | 2.50 |
| Glycerine | 10.00 |
| Sodium Fluoride | 0.05 |
| Sodium Lauryl Sulfate | 0.20 |
| TCHE | 0.06 |
| Flavor oil | 0.40 |
| Water Q.S. to | 100.00 |

EXAMPLE 4

Lozenge 75-80% Sugar
1-20% Corn Syrup
0.1-1.0 Flavor Oil
2% Tetrasodium Pyrophosphate
2.50% Gantrez S-97
0.01 to 0.05% NaF
0.01 to 0.1% TCHE
1 to 5% Magnesium Stearate Lubricant
0.01 to 0.2% Water

EXAMPLE 5

| Chewing Gum | Parts |
| --- | --- |
| Gum Base | 25.00 |
| Sorbitol (70%) | 17.00 |
| TCHE | 0.50 to 0.10 |
| Tetrasodium Pyrophosphate | 2.00 |
| Gantrez S.97 | 2.50 |

EXAMPLE 6

| Chewing Gum | Parts |
| --- | --- |
| Gum Base | 30.00 |
| TCHE | 0.50 |
| Gantrez | 2.00 |
| NaF | 0.05 |
| Glycerine | 0.50 |
| Crystalline Sorbitol | 53.00 |
| Flavor Oil and Water Q.S. to | 100.00 |

In the foregoing Examples improved results are also achievable when TCHE is replaced with each of phenol, 2,2'-methylene bis(4-chloro-6-Bromophenol), eugenol and thymol, and/or when Gantrez is replaced by other AEA's such as Carbopols (e.g. 934), or styrene phosphonic acid polymers having molecular weights within the range of about 3,000 to 10,000 such as poly (beta-styrenephosphonic acid), copolymers of vinyl phosphonic acid with beta-styrenephosphonic acid, and poly (alpha-styrenephosphonic acid), or sulfoacrylic oligomers, or a 1:1 copolymer of maleic anhydride with ethyl acrylate.

This invention has been described with respect to certain preferred embodiments and it will be understood that modifications and variations thereof obvious to those skilled in the art are to be included within the purview of this application and the scope of the appended claims.

We claim:

1. An oral composition comprising an orally acceptable aqueous-humectant dentifrice or toothpaste vehicle, a dentally acceptable water-insoluble polishing agent, a water-soluble or swellable anti-bacterial enhancing agent which is effective to enhance the anti-bacterial effect of a substantially water-insoluble non-cationic antibacterial agent, which contains at least one delivery-enhancing functional group and at least one organic retention-enhancing group, wherein said delivery-enhancing group enhances delivery of said antibacterial agent to oral tooth and gum surfaces and said retention-enhancing group enhances attachment adherence or bonding of said antibacterial agent on oral tooth and gum surfaces, and an effective anticalculus amount of a linear molecularly dehydrated polyphosphate, wherein the polyphosphate is present in amount such that the weight ratio of polyphosphate ion to anti-bacterial agent ranges from in excess of 0.72:1 to less than 4:1 said dentifrice or toothpaste having an optimized antiplaque effectiveness by presentation of said non-cationic antibacterial agent in a macroemulsion formed by adding said "A.E.A", or antibacterial enhancing agent incrementally, to a clear solution micro-emulsion of said antibacterial agent typically dissolved in admixtures of humectant and surface active agent, until the solution becomes cloudy, and may be characterized as a macroemulsion.

2. An oral composition comprising an orally acceptable aqueous-humectant dentifrice or toothpaste vehicle, a dentally acceptable water-insoluble polishing agent, a water-insoluble or swellable anti-bacterial-enhancing agent which is effective to enhance the anti-bacterial effect of a substantially water-insoluble non-cationic antibacterial agent, which contains at least one delivery-enhancing functional group and at least one organic retention-enhancing group, wherein said delivery-enhancing group enhances delivery of said antibacterial agent to oral tooth and gum surfaces and said retention-enhancing group enhances attachment, adherence or bonding of said antibacterial agent on oral tooth and gum surfaces, the said composition containing a mixture of potassium and sodium salts at least one of which is present in an effective anticalculus amount as a polyphosphate anticalculus agent, the ratio of potassium to sodium in the said composition being in the range of up to less than 3:1 said dentifrice or toothpaste having an optimized antiplaque effectiveness by presentation of said non-cationic antibacterial agent in a macroemulsion formed by adding said "A.E.A", or antibacterial enhancing agent incrementally, to a clear solution micro-emulsion of said antibacterial agent typically dissolved in admixtures of humectant and surface active agent, until the solution becomes cloudy, and may be characterized as a macroemulsion.

3. An oral composition comprising an orally acceptable aqueous-humectant dentifrice or toothpaste vehicle, a dentally acceptable water-insoluble polishing agent, substantially water insoluble non-cationic antibacterial agent in an amount which retards the oral growth of plaque of from 0.25% to less than 0.5% by weight and a water-soluble or swellable anti-bacterialenhancing agent which contains at least one delivery-enhancing functional group and at least one organic retention-enhancing group, wherein said delivery-enhancing group enhances delivery of said antibacterial agent to oral tooth and gum surfaces and said retention-enhancing group enhances attachment, adherence or bonding of said antibacterial agent on oral tooth and gum surfaces said dentifrice or toothpaste having an optimized antiplaque effectiveness by presentation of said non-cationic antibacterial agent in a macroemulsion formed by adding said "A.E.A", or antibacterial enhancing agent incrementally, to a clear solution microemulsion of said antibacterial agent typically dissolved in admixtures of humectant and surface active agent, until the solution becomes cloudy, and may be characterized as a macroemulsion.

4. An oral composition comprising an orally acceptable aqueous-humectant dentifrice or toothpaste vehicle, a dentally acceptable water-insoluble polishing agent, a substantially water insoluble non-cationic antibacterial agent, in an amount which retards the oral growth of plaque of from 0.25% to 0.35% and a water-soluble or swellable antibacterial-enhancing agent which contains at least one delivery-enhancing functional group and at least one organic retention-enhancing group, wherein said delivery-enhancing group enhances delivery of said antibacterial agent to oral tooth and gum surfaces and said retention-enhancing group enhances attachment, adherence or bonding of said antibacterial agent on oral tooth and gum surfaces said dentifrice or toothpaste having an optimized antiplaque effectiveness by presentation of said non-cationic antibacterial agent in a macroemulsion formed by adding said "A.E.A", or antibacterial enhancing agent incrementally, to a clear solution micro-emulsion of said antibacterial agent typically dissolved in admixtures of humectant and surface active agent, until the solution becomes cloudy, and may be characterized as a macroemulsion.

5. An oral composition comprising an orally acceptable aqueous-humectant dentifrice or toothpaste vehicle, a dentally acceptable water-insoluble siliceous polishing agent, about 0.25% to less than 0.5% by weight 9 f a substantially water-insoluble non-cationic anti-bacterial agent to retard oral growth of plaque and a water-soluble or swellable anti-bacterial-enhancing agent which contains at least one delivery-enhancing functional group and at least one organic retention-enhancing group, wherein said delivery-enhancing group, enhances delivery of said antibacterial agent to oral tooth and gum surfaces and said retention-enhancing group enhances attachment, adherence or bonding of said antibacterial agent on oral tooth and gum surfaces said dentifrice or toothpaste having an optimized antiplaque effectiveness by presentation of said non-cationic anti-bacterial agent in a macroemulsion formed by adding said "A.E.A", or antibacterial enhancing agent incrementally, to a clear solution micro-emulsion of said antibacterial agent typically dissolved in admixtures of humectant and surface active agent, until the solution becomes cloudy, and may be characterized as a macro-emulsion.

6. An oral composition comprising in an orally acceptable aqueous humectant dentifrice or toothpaste vehicle, a dentally acceptable water-insoluble polishing agent, an effective anticalculus amount of linear molecularly dehydrated polyphosphate salt anticalculus agent present in a mixture of sodium and potassium salts wherein the ratio of potassium to sodium in said composition is up to less than 3:1, and effective antiplaque amount to retard the oral growth of plaque of a substantially water insoluble non-cationic antibacterial agent and about 0.05-4% by weight of an antibacterial-enhancing agent which contains at least one delivery-enhancing functional group and at least one organic retention-enhancing group, wherein said delivery-enhancing group enhances delivery of said antibacterial agent to oral tooth and gum surfaces and said retention-enhancing group enhances attachment, adherence or bonding of said antibacterial agent on oral tooth and gum surfaces said dentifrice or toothpaste having an optimized antiplaque effectiveness by presentation of said non-cationic antibacterial agent in a macroemulsion formed by adding said "A.E.A", or antibacterial enhancing agent incrementally, to a clear solution micro-emulsion of said antibacterial agent typically dissolved in admixtures of humectant and surface active agent, until the solution becomes cloudy, and may be characterized as a macroemulsion.

7. A composition according to claim 6 wherein the ratio of potassium to sodium is from 0.37:1 to 1.04:1.

8. An oral composition comprising an orally acceptable aqueous-humectant dentifrice or toothpaste vehicle, a dentally acceptable water-insoluble polishing agent, an effective amount of a linear, molecularly dehydrated polyphosphate, an effective amount to retard the growth of plaque in the range of about 0.01-5% by weight of a substantially water insoluble non-cationic antibacterial agent and about 0.05-4% by weight of water-soluble or swellable antibacterial-enhancing agent which contains at least one delivery-enhancing functional group and at least one organic retention-enhancing group, wherein said delivery-enhancing group enhances delivery of said antibacterial agent to oral tooth and gum surfaces and said retention-enhancing group enhances attachment, adherence or bonding of said antibacterial agent on oral tooth and gum surfaces, wherein said polyphosphate is present in an amount wherein the weight ratio of said antibacterial enhancing agent to said polyphosphate ion ranges from about 1:6 to about 2.7:1 said dentifrice or toothpaste having an optimized antiplaque effectiveness by presentation of said non-cationic antibacterial agent in a macroemulsion formed by adding said "A.E.A", or antibacterial enhancing agent incrementally, to a clear solution micro-emulsion of said antibacterial agent typically dissolved in admixtures of humectant and surface active agent, until the solution becomes cloudy, and may be characterized as a macro-emulsion.

9. The oral composition claimed in claim 8 wherein said antibacterial agent is selected from the group consisting of halogenated diphenyl ethers, halogenated salicylanilides, benzoic esters, halogenated carbanilides and phenolic compounds.

10. The oral composition claimed in claim 9 wherein said antibacterial agent is a halogenated diphenyl ether.

11. The oral composition claimed in claim 10 wherein said halogenated diphenyl ether is 2,4,4'-trichloro-2'-hydroxyphenyl ether.

12. The oral composition claims in any of claims 8 to 11 wherein said amount of antibacterial agent is about 0.25-0.5%.

13. The oral composition claimed in any of claims 8 to 11 wherein said linear molecularly dehydrated polyphosphate salt is an alkali metal pyrophosphate.

14. The oral composition claimed in claim 13 wherein said alkali metal pyrophosphate is tetrasodium pyrophosphate.

15. The oral composition claimed in any of claims 8 to 11 wherein said polyphosphate is present in amount of about 1-2.5% by weight.

16. The oral composition claimed in any of claims 8 to 11 wherein the weight ratio of antibacterial enhancing agent to polyphosphate ion is about 1.7:1 to about 2.3:1.

17. The oral composition claimed in claim 16 wherein said weight ratio is about 1:9 to about 2:1.

18. The oral composition claimed in any of claims 8 to 11 wherein said vehicle comprises water, humectant and a gelling agent.

19. The oral composition according to any of claims 8 to 11 wherein said antibacterial-enhancing agent has an average molecular weight of about 100 to about 1,000,000.

20. The oral composition according to claim 19 wherein said delivery-enhancing group is acidic.

21. The oral composition according to claim 20 wherein said delivery-enhancing group is selected from the group consisting of carboxylic, phosphoric, phosphinic, and sulfonic acids, and salts, and mixtures thereof and wherein said organic retention-enhancing group comprises the formula $-(X)_n-R$ wherein X is O, N, S, SO, $SO_2$, P, PO or Si, R is hydrophobic alkyl, aryl, alkaryl, alkenyl, acyl, aralkyl, heterocyclic, or inert-substituted derivatives thereof, and n is zero or 1 or more and wherein said antibacterial-enhancing agent is a natural or synthetic monomer or a polymer selected from the group consisting of oligomers, homopolymers, copolymers of two or more monomers, ionomers, block copolymers, graft copolymers and cross-linked polymers and monomers.

22. The oral composition claimed in claim 21 wherein said antibacterial-enhancing agent is an anionic polymer containing a plurality of said delivery-enhancing and retention-enhancing groups.

23. The oral composition claimed in claim 22 wherein said anionic polymer comprises a chain containing repeating units each containing at least one carbon atom.

24. The oral composition claimed in claim 23 wherein the unit contains at least one delivery-enhancing group and at least one retention-enhancing group bonded to the same, vicinal, or other atoms in the chain.

25. The oral composition claimed in claim 24 wherein the delivery-enhancing group is a carboxylic group of salt thereof.

26. An oral composition comprising in an orally acceptable aqueous humectant dentifrice or toothpaste vehicle, a dentally acceptable water-insoluble polishing agent, an effective anticalculus amount of a linear molecularly dehydrated polyphosphate, an effective antiplaque amount of a substantially water insoluble noncationic antibacterial agent, in the range of about 0.01-5% by weight, and about 0.05-4% by weight of an anionic copolymer of maleic acid or anhydride with another ethylenically unsaturated polymerizable monomer, which copolymer enhances delivery and attachment, adherence or bonding of said antibacterial agent on oral tooth and gum surfaces, wherein said polyphosphate is present in amount wherein the weight ratio of said antibacterial enhancing agent to said polyphosphate ranges from about 1:6 to about 2.7:1 said dentifrice or toothpaste having an optimized antiplaque effectiveness by presentation of said non-cationic antibacterial agent in a macroemulsion formed by adding said "A.E.A", or antibacterial enhancing agent incrementally, to a clear solution micro-emulsion of said antibacterial agent typically dissolved in admixtures of humectant and surface active agent, until the solution becomes cloudy, and may be characterized as a macroemulsion.

27. The oral composition claimed in claim 26 wherein said other monomer of said copolymer is methyl vinyl ether in a 4:1 to 1:4 molar ratio with the maleic acid or anhydride.

28. The oral composition claimed in either of claims 26 or 27 wherein said copolymer has a molecular weight of about 30,000-1,000,000.

29. The oral composition claimed in claim 28 wherein the copolymer has an average molecular weight of about 70,000.

30. The oral composition claimed in any of claims 8 to 11 containing a fluoride-providing source.

31. The oral composition claimed in claim 1 wherein said weight ratio ranges from 1:1 to 3.5:1.

32. The oral composition claimed in claim 31 wherein said ratio ranges from about 1.6:1 to 2.7:1.

33. The oral composition claimed in claim 2 wherein said ratio is in the range from 0.37:1 to 1.04:1.

* * * * *

UNITED STATES PATENT AND TRADEMARK OFFICE
CERTIFICATE OF CORRECTION

PATENT NO. : 5,292,526
DATED : March 8, 1994
INVENTOR(S) : Abdul Gaffar, Nuran Nabi, John Afflitto and Orum Stringer It is certified that error appears in the above-identified patent and that said Letters Patent is hereby corrected as shown below:

Column 2, line, 43-44, cancel "polyphosphate ion to antibacterial enhancing agent" and insert --antibacterial enhancing agent to polyphosphate ion--.

Column 12, line 59, after "546-573" cancel "or" and insert --of--.

Column 19, cancel lines 46-55 (entire Example 6).

Signed and Sealed this

First Day of April, 1997

*Attest:*

BRUCE LEHMAN

*Attesting Officer*     *Commissioner of Patents and Trademarks*